US00PP33819P3

(12) United States Plant Patent
Post

(10) Patent No.: US PP33,819 P3
(45) Date of Patent: Jan. 4, 2022

(54) ***CHRYSANTHEMUM* PLANT NAMED 'DLFRADO2'**

(50) Latin Name: ***Chrysanthemum* X *morifolium***
Varietal Denomination: DLFRADO2

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 17/170,586

(22) Filed: Feb. 8, 2021

(65) Prior Publication Data

US 2021/0251119 P1 Aug. 12, 2021

Related U.S. Application Data

(60) Provisional application No. 62/995,750, filed on Feb. 12, 2020.

(51) Int. Cl.
*A01H 5/02* (2018.01)
*A01H 6/14* (2018.01)

(52) U.S. Cl.
USPC ..... Plt./294
CPC ..... *A01H 6/1424* (2018.05)

(58) Field of Classification Search
USPC ..... Plt./294
See application file for complete search history.

*Primary Examiner* — Annette H Para
(74) *Attorney, Agent, or Firm* — C. Anne Whealy

(57) ABSTRACT

A new and distinct cultivar of *Chrysanthemum* plant named 'DLFRADO2', characterized by its upright plant habit; uniform growth habit; dark green-colored leaves; uniform and freely flowering habit; strong upright flowering stems; spray-type inflorescences with bright yellow-colored ray florets and vivid yellow-colored disc florets; resistance to Fusarium; relative tolerance to high temperatures; and good postproduction longevity.

2 Drawing Sheets

Figure 1:
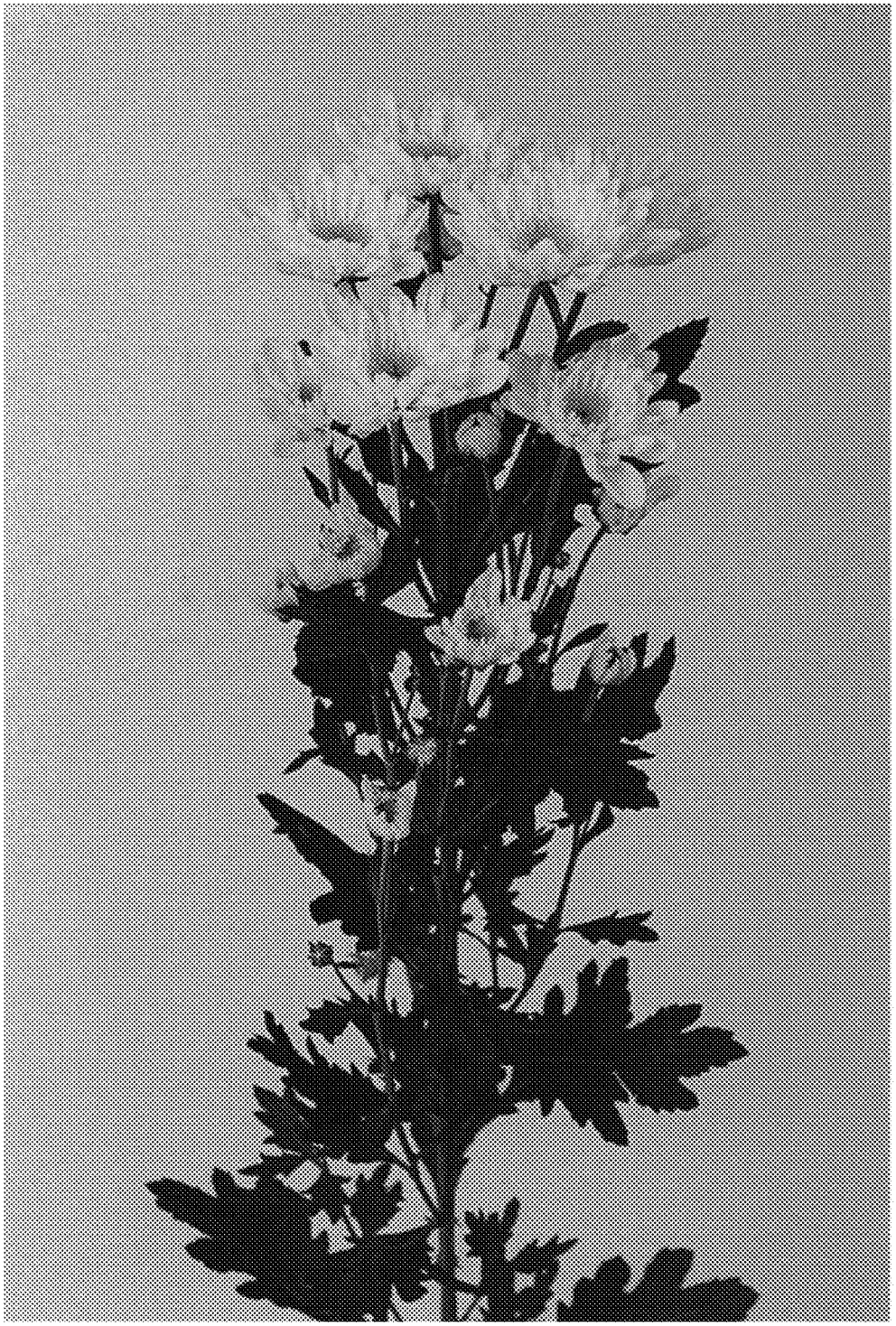

Botanical designation: *Chrysanthemum* X *morifolium*.
Cultivar denomination: 'DLFRADO2'.

CROSS-REFERENCED TO CLOSELY-RELATED APPLICATIONS

Title: Varieties of *Chrysanthemum* Plants
Inventor/Applicant: Arie Gerard Post
Filed: Feb. 12, 2020
Ser. No.: 62/995,750
Inventor/Applicant hereby claims the benefit of this provisional U.S. Patent Application.

STATEMENT REGARDING PRIOR DISCLOSURES BY INVENTOR/APPLICANT & ASSIGNEE

An European Community Plant Breeder's Rights application for the instant plant was filed by the Assignee, Deliflor Royalties B.V. of Maasdijk, The Netherlands on Jul. 29, 2019, application number 2019/1847.

A Mexican Plant Breeder's Rights application for the instant plant was filed by the Assignee, Deliflor Royalties B.V. of Maasdijk, The Netherlands on Nov. 14, 2019, application number 3062.

A Columbian Plant Breeder's Rights application for the instant plant was filed by the Assignee, Deliflor Royalties B.V. of Maasdijk, The Netherlands on Jun. 24, 2020, application number A202686.

A South African Plant Breeder's Rights application for the instant plant was filed by the Assignee, Deliflor Royalties B.V. of Maasdijk, The Netherlands on Sep. 3, 2020, application number PT 9275.

A Malaysian Plant Breeder's Rights application for the instant plant was filed by the Assignee, Deliflor Royalties B.V. of Maasdijk, The Netherlands on Sep. 29, 2020, application number PVBT 047/20.

Foreign priority is not claimed to any of these applications.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFRADO2'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'Deliradost', not patented. The new *Chrysanthemum* plant was discovered and selected as a single flowering plant from within a population of plants of 'Deliradost' in a controlled greenhouse environment in Maasdijk, The Netherlands in July, 2013.

Asexual reproduction of the new *Chrysanthemum* plant by vegetative terminal cuttings since July, 2013 in a controlled greenhouse environment in Maasdijk has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFRADO2'. These characteristics in combination distinguish 'DLFRADO2' as a new and distinct *Chrysanthemum* plant:

1. Upright plant habit; uniform growth habit.
2. Dark green-colored leaves.
3. Uniform and freely flowering habit.
4. Strong upright flowering stems.
5. Spray-type inflorescences with bright yellow-colored ray florets and vivid yellow-colored disc florets.
6. Resistant to Fusarium.
7. Relatively tolerant to high temperatures.
8. Good postproduction longevity.

Plants of the new *Chrysanthemum* differ primarily from plants of the mutation parent, 'Deliradost', in ray floret color as ray florets of plants of the new *Chrysanthemum* are bright yellow in color whereas ray florets of plants of 'Deliradost' are white in color. In addition, plants of the new *Chrysanthemum* flower about three days later than plants of 'Deliradost'.

Plants of the new *Chrysanthemum* can be compared to plants of *Chrysanthemum* X *morifolium* 'Radost Yellow', not patented. In side-by-side comparisons, plants of the new *Chrysanthemum* differ primarily from plants of 'Radost Yellow' in disc florets as inflorescences of plants of the new *Chrysanthemum* have larger discs than inflorescences of plants of 'Radost Yellow'. In addition, plants of the new *Chrysanthemum* flower about four days earlier than plants of 'Radost Yellow'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) comprises a side perspective view of a typical flowering stem of 'DLFRADO2' grown as a spray-type cut flower.

Figure 2:
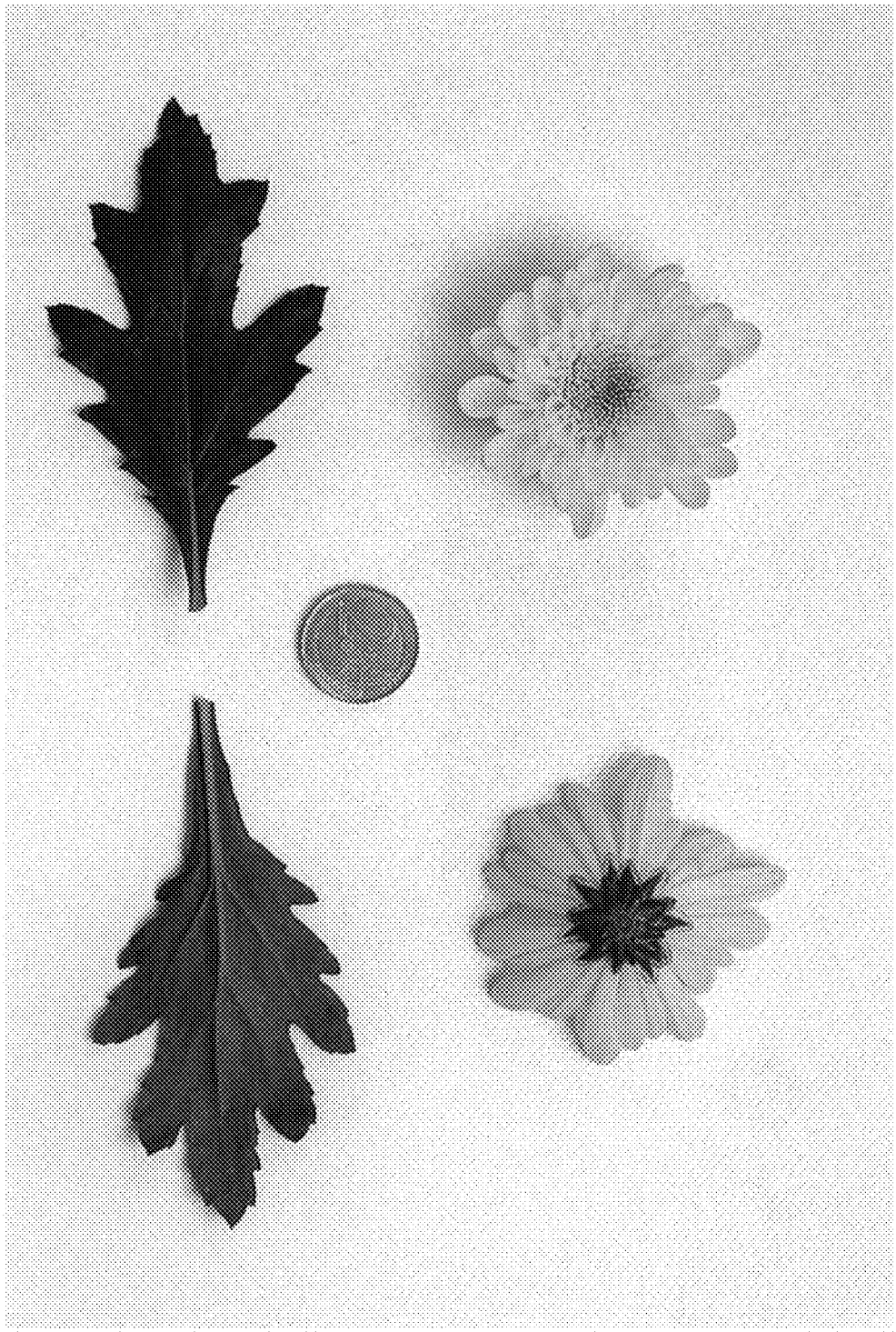

The photograph on the second sheet (FIG. 2) is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were eleven weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFRADO2'.

Parentage: Naturally-occurring whole plant mutation of *Chrysanthemum* x *morifolium* 'Deliradost', not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem spray-type; upright plant habit; vigorous growth habit and rapid growth rate.

*Plant height, soil level to top of foliar plane*.—About 78.9 cm.

*Plant height, soil level to top of inflorescence plane*.—About 83.7 cm.

*Plant (spray) diameter*.—About 18.3 cm.

*Flowering stem length*.—About 75.3 cm.

*Flowering stem diameter*.—About 7 mm.

*Flowering stem internode length*.—About 2.4 cm.

*Flowering stem strength*.—Strong.

*Flowering stem aspect*.—Erect.

*Flowering stem texture and luster*.—Moderately to densely pubescent; slightly glossy.

*Flowering stem color, developing*.—Close to 144A.

*Flowering stem color, developed*.—Close to 144A and at the nodes, close to 143A.

*Leaf description*.—Arrangement: Alternate; simple. Length: About 11.2 cm. Width: About 6.6 cm. Shape, in outline: Ovate to oblong. Apex: Abruptly acute, minute. Base: Attenuate. Margin: Palmately lobed, coarsely serrate to dentate; sinuses divergent and medium to deep in depth. Texture and luster, upper surface: Moderately pubescent, not rugose; moderately velvety; slightly glossy. Texture and luster, lower surface: Densely pubescent, prominent venation; slightly velvety; very slightly glossy. Venation pattern: Pinnate, reticulate. Color: Developing leaves, upper surface: Close to 143A to 143B. Developing leaves, lower surface: Close to 144A. Fully developed leaves, upper surface: Close to 137A; venation, close to 146C. Fully developed leaves, lower surface: Close to between 138A and 147B; venation, close to 146D. Petioles: Length: About 2.2 cm. Diameter: About 2.75 mm by 4 mm. Strength: Moderately strong. Texture and luster, upper and lower surfaces: Moderately pubescent; moderately glossy. Color, upper surface: Close to 146B; edges, close to 137A to 137B. Color, lower surface: Close to 146D; edges, close to 137B to 137C. Stipules: Quantity and appearance: Two leafy stipules, opposite, at the petiole attachment to the stem. Length: About 2 mm. Width: About 0.2 mm. Shape, in outline: Deltoid. Texture and luster, upper surface: Moderately pubescent; slightly glossy. Texture and luster, lower surface: Densely pubescent; very slightly glossy. Color: Upper surface: Close to 137A; venation, close to 146C. Lower surface: Close to between 138A and 147B; venation, close to 146D.

Inflorescence description:

*Appearance*.—Spray-type inflorescence form with obovate-shaped ray florets and tubular disc florets; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 49 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a spray-type, about 31 inflorescences develop per flowering stem.

*Inflorescence size*.—Diameter, grown as a spray-type: About 6.5 cm. Depth (height), grown as a spray-type: About 2.4 cm. Disc diameter: About 2.4 cm.

*Receptacles*.—Height: About 4 mm. Diameter: About 4 mm. Shape: Broadly ovate. Color: Close to 145A.

*Inflorescence buds*.—Height: About 1 cm. Diameter: About 1.3 cm. Shape: Flattened globular to roughly globular. Texture and luster: Distally, smooth and glabrous; proximally, sparsely pubescent; moderately glossy. Color: Darker than 143A to 143C; immature ray florets, close to 2A to 2B.

*Ray florets*.—Quantity and arrangement: About 40 arranged in about two whorls. Length: About 3.1 cm, varying between 2.2 cm and 3.7 cm. Width: About 0.9 cm, varying between 0.7 cm and 1.1 cm. Shape: Obovate; moderately carinate. Apex: Obtuse to retuse. Base: Attenuate. Margin: Entire, strongly involute; not undulate. Aspect: About 30° to 40° from vertical. Texture and luster, upper surface: Smooth, glabrous; velvety; matte. Texture and luster, lower surface: Smooth, glabrous; slightly velvety; very slightly glossy. Color: When opening, upper surface: Close to 2A. When opening, lower surface: Close to 3B. Fully opened, upper surface: Close to 2A to slightly lighter than 2A; venation, similar to lamina color; color becoming closer to 2B to slightly lighter than 2B with development. Fully opened, lower surface: Close to 3C; venation, similar to lamina color; color does not change with development.

*Disc florets*.—Quantity and arrangement: About 190 massed at the center of the receptacle. Length: About 1.2 cm, varying between 0.5 cm and 1.7 cm. Diameter: About 3 mm, varying between 1 mm and 5 mm. Shape: Lower 85% fused into a tube; upper 15% free. Apex: Narrowly acute. Margin, free-part: Entire. Texture and luster, inner surface: Smooth, glabrous; moderately velvety; matte. Texture and luster, outer surface: Smooth, glabrous; velvety; very slightly glossy. Color, when opening, inner and outer surfaces: Close to 145C; towards the apex, close to N144B. Color, fully opened, inner surface: Close to 2A. Color, fully opened, outer surface: Close to 3B.

*Involucral bracts*.—Quantity and arrangement: About 16 arranged in about two whorls. Length: About 1 cm. Width: About 4.5 mm. Shape: Ovate to narrowly ovate. Apex: Obtuse. Base: Cuneate. Margin: Entire. Texture and luster, upper surface: Smooth, glabrous; glossy. Texture and luster, lower surface: Sparsely to moderately pubescent; matte. Color, upper surface: Close to 143A; lateral margins, translucent and close to 157D and apical margins slightly tinged with close to N199A. Color, lower surface: Close to 137B to 137C; towards the apex, close to NN137B; lateral margins, translucent and close to 157D and apical margins slightly tinged with close to N199A.

*Peduncles*.—Length, terminal peduncle: About 3.9 cm. Diameter, terminal peduncle: About 3.5 mm. Length, third peduncle: About 6.5 cm. Diameter, third peduncle: About 3 mm. Strength: Strong. Aspect, terminal peduncle: Upright. Aspect, third peduncle: About 30° from the flowering stem axis. Texture and luster: Densely pubescent; slightly glossy. Color: Close to 138A to 138B.

*Reproductive organs*.—Androecium: Present on disc florets only. Quantity: About five per floret. Filament length: About 2 mm. Filament color: Close to 150C. Anther size: About 0.5 mm by 1 mm. Anther shape: Narrowly oblong. Anther color: Close to 164C. Pollen amount: None observed. Gynoecium: Present on both ray and disc florets. Quantity: One per floret. Pistil length: About 7 mm. Style length: About 6.5 mm. Style color: Close to 145C to 145D. Stigma diameter: About 1 mm. Stigma shape: Cleft, decurrent. Stigma color: Close to 151D. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to Fusarium Wilt (*Fusarium oxysporum* spp. *chrysanthemi* (strain FoNL1)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFRADO2' as illustrated and described.

* * * * *